(12) United States Patent
Buchholz et al.

(10) Patent No.: US 6,433,227 B1
(45) Date of Patent: Aug. 13, 2002

(54) USE OF TRIS (TRIFLUORO METHYLSULFONYL) METHANE, IN ADDITION TO ALKALINE METAL SALTS AND ALKALINE-EARTH METAL SALTS THEREOF AS CATALYSTS DURING C-C BONDING SYNTHESES AND THE NOVEL MG SALT OF TRIS (TRIFLUORO METHYLSULFONYL) METHANE

(75) Inventors: Herwig Buchholz, Frankfurt; Klaus-Dieter Franz, Kelkheim; Herbert Mayr, Starnberg; Marcus-Alexander Funke, Darmstadt; Andrea Zehetner, Munich, all of (DE)

(73) Assignee: Merck Patent Gesellschaft mit beschraenkter Haftung (DE)

( * ) Notice: Subject to any disclaimer, the term of this patent is extended or adjusted under 35 U.S.C. 154(b) by 0 days.

(21) Appl. No.: 09/529,008

(22) PCT Filed: Oct. 5, 1998

(86) PCT No.: PCT/EP98/06326

§ 371 (c)(1),
(2), (4) Date: Apr. 6, 2000

(87) PCT Pub. No.: WO99/17878

PCT Pub. Date: Apr. 15, 1999

(30) Foreign Application Priority Data

Oct. 6, 1997 (DE) ......................................... 197 43 985

(51) Int. Cl.$^7$ .......................... C07C 45/00; C07C 41/00
(52) U.S. Cl. ....................... 568/312; 568/309; 568/626; 568/631
(58) Field of Search ................................ 502/152, 155, 502/150, 151, 153, 168, 171; 522/25, 29; 568/626, 631, 309, 312; 564/1, 305, 336; 560/51; 585/600; 556/400

(56) References Cited

U.S. PATENT DOCUMENTS 5,554,664 A * 9/1996 Lamanna et al. ............. 522/25

OTHER PUBLICATIONS

Chemical Abstracts, vol. 109, No. 1, Jul. 4, 1988; abstract No. 6063p Turowsky L.; Tris (trifluoromethyl) suldonyl-!methane, HC (s020CF3)3 p. 572: Spalte 2; & Inorg Chem., BD. 27, Nr. 12, Seiten 2135–2137.

* cited by examiner

Primary Examiner—Samuel Barts
Assistant Examiner—Elvis O. Price
(74) Attorney, Agent, or Firm—Millen, White, Zelano & Branigan, P.C.

(57) ABSTRACT

Compounds are used as catalysts according to general formula (1) $M^{+x}(C(SO_2CF_3)_3)_x$, whereby x is equal to 1 or 2; M represents one hydrogen or alkaline metal atom when x equals 1; and M represents one alkaline-earth metal atom when x equals 2. The invention also relates to a novel Mg compound of formula (1).

18 Claims, No Drawings

USE OF TRIS (TRIFLUORO METHYLSULFONYL) METHANE, IN ADDITION TO ALKALINE METAL SALTS AND ALKALINE-EARTH METAL SALTS THEREOF AS CATALYSTS DURING C-C BONDING SYNTHESES AND THE NOVEL MG SALT OF TRIS (TRIFLUORO METHYLSULFONYL) METHANE

The invention relates to the use of tris (trifluoromethylsulfonyl)methane and its alkali metal salts and alkaline earth metal salts as catalysts in the reaction of Lewis-acid-activatable or Brönsted-acid-activatable electrophiles with nucleophiles or for carrying out [4+2]-cycloadditions, and to the provision of the novel Mg salt of tris(trifluoromethylsulfonyl)methane.

The Lewis-acid-induced reaction of electrophiles, for example alkyl chlorides or carbonyl compounds, with nucleophiles is a simple, widely used and long-known synthesis method for building up carbon skeletons.

The metal halides $MX_n$ used here as Lewis acids, for example $TiCl_4$, $ZnCl_2$ or $AlCl_3$ are frequently, as in the case of Friedel-Crafts acylations, used in equimolar amounts and must be irreversibly deactivated by hydrolysis during the work-up of the reaction batches. This produces large amounts of unutilizable wastes. However, carrying out industrial-scale syntheses in which unutilizable byproducts are formed is highly problematical from the ecological and economic aspects. Reutilizable Lewis acid systems and their use in Lewis-acid-induced carbon-carbon bond formations is, if possible, to be given preference.

Reusable Lewis acid systems in carbon-carbon bond-forming syntheses are, for example, lithium perchlorate or magnesium perchlorate in strongly coordinating organic solvents, such as diethyl ether, or in non-coordinating solvents, such as dichloromethane.

In this case the solutions of lithium perchlorate or magnesium perchlorate in diethyl ether show a sufficient ionization capacity in order to partially ionize, for example trityl chloride, in order to achieve the desired reaction, the ionization capacity increasing with increasing lithium salt concentration (cf. Y. Pocker, R. F. Buchholz, J. Am. Chem. Soc. 1970, 92, 2075–2084). The strong coordinating interaction between the lithium cation and the solvent diethyl ether favour, however, the formation of etherates and therefore decrease considerably the Lewis acidity of the lithium cation (Y. Pocker et al., loc. cit.). Therefore, the pronounced Lewis acid properties of lithium perchlorate solutions are restricted in ether to highly concentrated solutions. Such solutions are used, in particular, in the catalysis of Diels-Alder reactions with substances sensitive to hydrolysis, in which case as an additional effect the formation of the endo-cycloadducts is promoted.

Although the solubility of lithium perchlorate in non-coordinating solvents such as dichloromethane is very low (solubility $<<10^{-3}$ mol/l), a suspension of lithium perchlorate in dichloromethane also has Lewis acid properties. Aldehydes are sufficiently activated in this heterogeneous medium, for example, for reactions with 1-tert-butyldimethylsiloxy-1-methoxyethene to give the corresponding β-siloxycarboxylic esters (Mukaiyama-aldol reaction), in which case lithium perchlorate is used in catalytic amounts with respect to the starting materials.

However, the use of lithium perchlorate and magnesium perchlorate as Lewis acids in the organic synthesis is a considerable hazard potential, which is due firstly to the redox instability of the perchlorates (risk of decomposition and explosion) and secondly to the formation of organic perchlorates which cannot be safely excluded in the reaction to be catalyzed (P. G. Urben, Chemtech 1991 (5), 259; A. B. Charette in Encyclopedia of Reagents for Organic Synthesis (Edited by L. A. Paquette), J. Wiley and Sons, New York 1995, Vol. 5, p. 3155). The use of perchlorates as Lewis acids in industrial synthesis is therefore a problem. Although it is possible to recover lithium perchlorate or magnesium perchlorate from the organic reaction solvents, such as ether, dichloromethane or pentane, in principle by aqueous extraction, the crystallization of the perchlorates from water is in turn associated with the above-described risks and also with a high energy consumption, so that the work-up is unfavourable for safety and economic reasons.

The object therefore underlying the present invention is to provide Lewis acid catalysts for the reaction of electrophiles with nucleophiles, which catalysts can be used safely industrially and can be recovered readily and safely without a high energy consumption.

This object is achieved by using at least one compound of formula (1)

where x is 1 or 2,
M is a hydrogen atom or alkali metal atom when x is 1, or an
alkaline earth metal atom when x is 2, as catalyst.

The preparation of tris(trifluoromethylsulfonyl)methane and also of certain alkali metal and alkaline earth metal tris(trifluoromethylsulfonyl)methanides of the formula (1) is known and described in L. Turowski, K. Seppelt, Inorg. Chem. 1988, 27, 2135–2137; K. Seppelt, Angew. Chem. 1993, 105, 1074–1076 and in J. Org. Chem. Vol. 38, No. 19, pages 3358 ff. Tris(trifluoromethylsulfonyl)methane and its lithium salt and potassium salt are also disclosed by (Beilstein Registry Nos. 4767561, 5899593,. WO 92/FR1024).

The compounds of the formula (1) may, because of their low solubility in non-coordinating solvents, be removed simply by filtration from the reaction batches. Since the compounds of the formula (1) are distinguished by high redox stability and thermal stability, syntheses using these salts and their recovery from the reaction batches have a markedly lower hazard potential than analogous reactions using inorganic perchlorates.

The compound of the formula (1) preferably used is the acid itself (M=H), the lithium, potassium, magnesium or calcium salts, and in particular the lithium and magnesium salts.

The compounds of the formula (1) are used in homogeneous solution in a coordinating organic solvent, for example diethyl ether, THF or dioxane. The concentration of the compound (1) is in this case in catalytic amounts, preferably in the range from 0.01 to 0.1 mol/l, in particular 0.02–0.04 mol/l.

It is also possible to use the compounds of the formula (1) as a suspension in non-coordinating organic solvents, for example dichloromethane, chloroform, carbon tetrachloride or hydrocarbons, such as n-hexane, n-pentane, preferably dichloromethane.

Based on electrophile, 0.01–10 mol %, preferably 0.5–6 mol %, of a compound of the formula (1) can be used.

Using the compounds of the formula (1), Lewis-acid-induced or Brönsted-acid-induced carbon-carbon bond-forming syntheses and [4+2] cycloadditions of any type can be catalysed.

In order to obtain the resultant products at a sufficiently high yield and reasonable reaction rates, it is advantageous if not only the relative reactivity of the reacting electrophilic compounds towards the nucleophilic compounds but also the nucleophilicity N of the nucleophilic compounds used do not fall below certain minimum values.

The parameter N for the nucleophilicity of a compound was introduced by Mayr and Patz, Angew. Chem. 1994, 106, 990–1010.

For numerous nucleophilic compounds, the value N can be taken from this publication, in particular pages 1003–1004. Table 1 also contains a number of N values.

The relative reactivity of electrophilic compounds can be specified, inter alia, by using the ethanolysis rate constant $k_{EtOH}$, i.e. the solvolysis rate constant in 100% ethanol at 25° C.

This fundamental quantity can be used in particular for specifying the relative reactivity of alkyl halides, in particular alkyl chlorides or alkyl bromides. The corresponding values for $k_{EtOH}$ (25° C.) for numerous alkyl halides can be taken from, for example, the publication by J. P. Dau-Schmidt and H. Mayr in Chem. Ber. 1994, 127, pages 205–212, or the dissertation by J. P. Dau-Schmidt, Lübeck Medical University 1992.

Alkyl halides which are suitable here for a reaction of alkyl halides, in particular alkyl chlorides or alkyl bromides, induced by the lithium salt according to formula (1) in a suspension in non-coordinating organic solvents, preferably in dichloromethane, are those having a $k_{EtOH}$ (25° C.) value of $\geq 5 \times 10^{-5} s^{-1}$, or by the lithium salt according to formula (1) in a $\geq 0.03$ molar solution in coordinating organic solvents, preferably in diethyl ether, are alkyl halides, in particular alkyl chlorides or alkyl bromides, having $k_{EtOH} \geq 1 \times 10^{-3} s^{-1}$.

When the magnesium salt according to formula (1) is used suspended in non-coordinating organic solvents, preferably in dichloromethane, it is advantageous to use alkyl halides, in particular chlorides or bromides, having a $k_{EtOH}$ (25° C.) value of $\geq 1 \times 10^{-7} s^{-1}$.

The corresponding nucleophilic compounds reacting with the alkyl halides should in all cases have a value N of $\geq 1.62$.

Examples of alkyl halides, preferably alkyl chlorides or alkyl bromides, having the specified minimum values $k_{EtOH}$, but which do not represent an exhaustive listing, are alkyl halides where alkyl is preferably unbranched or branched $C_1$–$C_{10}$-alkyl which is unsubstituted or substituted at the a carbon atom by 1 to 3 identical or different radicals of any type, in particular by aryl, preferably $C_6$–$C_{10}$-aryl, substituted aryl, for example methoxyphenyl, tolyl, cumenyl, aminophenyl, di- or trialkylaminophenyl, $C_2$–$C_6$-alkenyl, for example 1-methyl-2-butenyl, $C_5$–$C_6$-cycloalkenyl, in particular cyclopentenyl, and 1,1-dimethyl-2-butynyl, 3-pentan-2-yl. Halide is fluoride, chloride, bromide or iodide, preferably chloride and bromide, particularly preferably chloride.

Hereinafter is set forth a tabulation (1.1.) of selected alkyl chlorides which can be used as possible reaction partners of allyltrimethylsilane or more reactive nucleophiles (N$\geq$1.62) in a suspension of $LiC(SO_2CF_3)_3$ in dichloromethane:

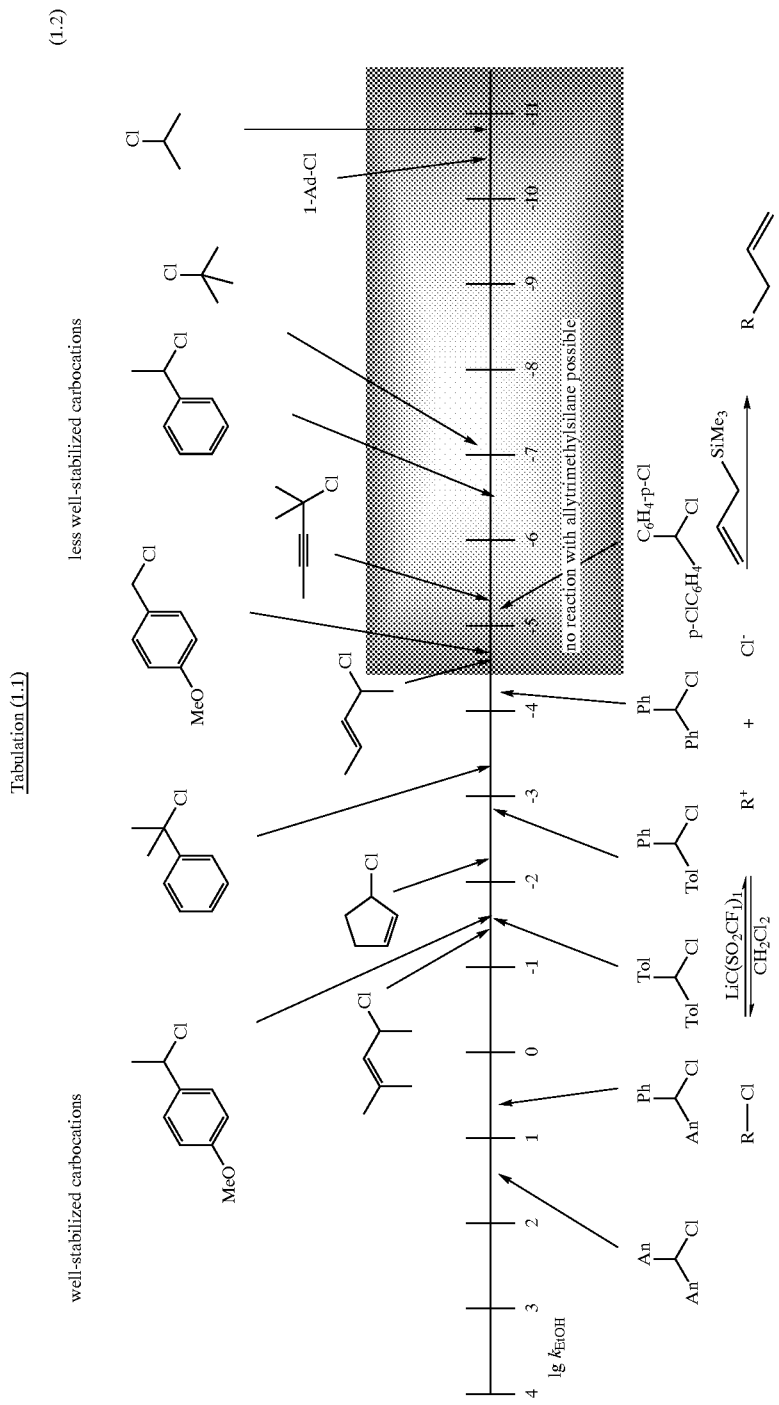

In accordance with the above reaction diagram (1.2), alkyl chlorides having an ethanolysis rate constant $k_{EtOH} \geq 5 \times 10^{-5}$ $s^{-1}$ give well-stabilized carbocations with the Li salts of the formula (1) used according to the invention and are therefore suitable for the reaction with nucleophilic compounds having a value $N \geq 1.62$.

Selected alkyl chlorides which, in a 0.03 M solution of $LiC(SO_2CF_3)_3$ in diethyl ether can be used as possible reaction partners of allyltrimethylsilane or more reactive nucleophiles ($N \geq 1.62$) may be taken from the tabulation (1.3) below:

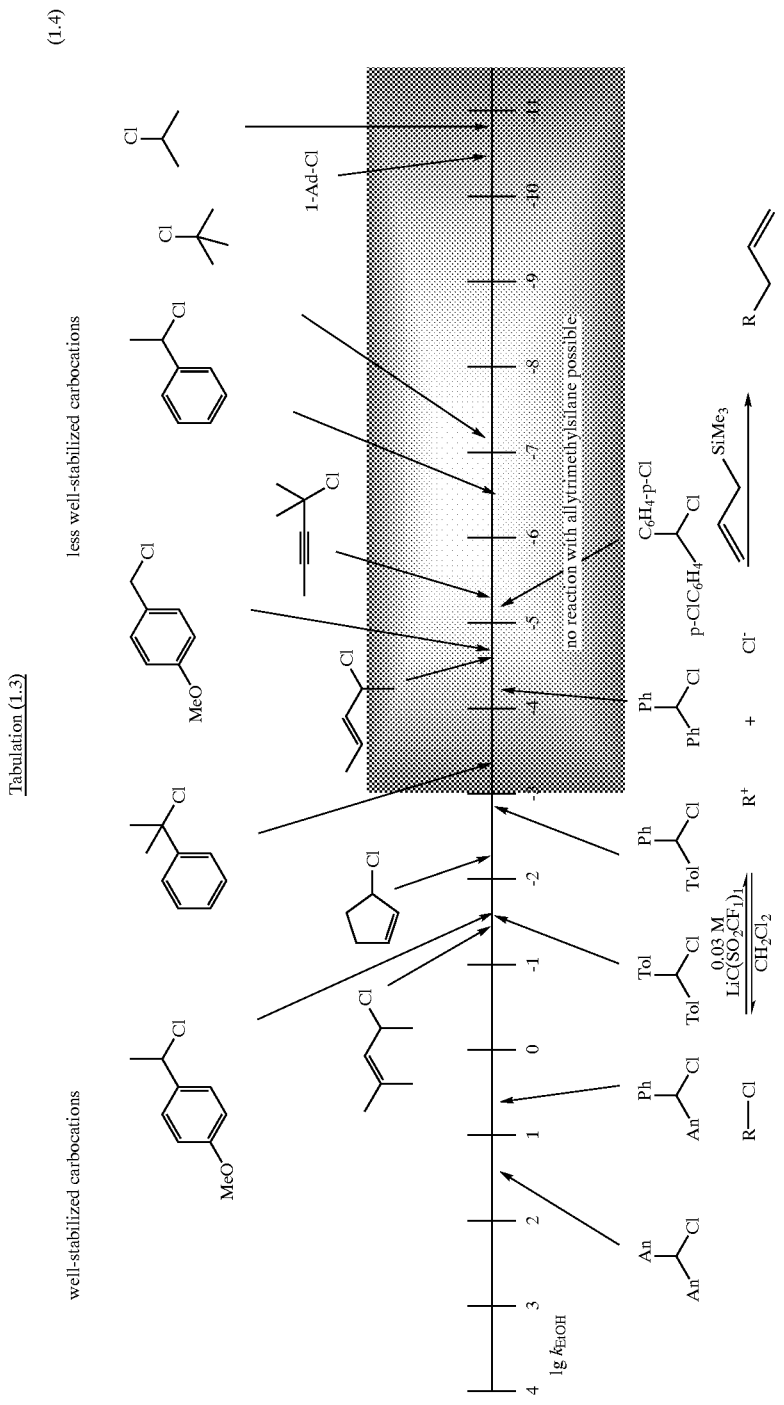

In accordance with the reaction diagram (1.4), alkyl chlorides with an ethanolysis rate constant $k_{EtOH}$ (25° C.)$\geq 1 \times 10^{-1}$, sal give, with the Li salts of the formula (1) used according to the invention, well-stabilized carbocations which can be reacted with nucleophilic compounds having $N \geq 1.62$.

Selected alkyl chlorides which, in a suspension of $Mg(C(SO_2CF_3)_3)_2$ in dichloromethane, can be used as possible reaction partners of allyltrimethylsilane or more reactive nucleophiles ($N \geq 1.62$) may be taken from the tabulation (1.5) below:

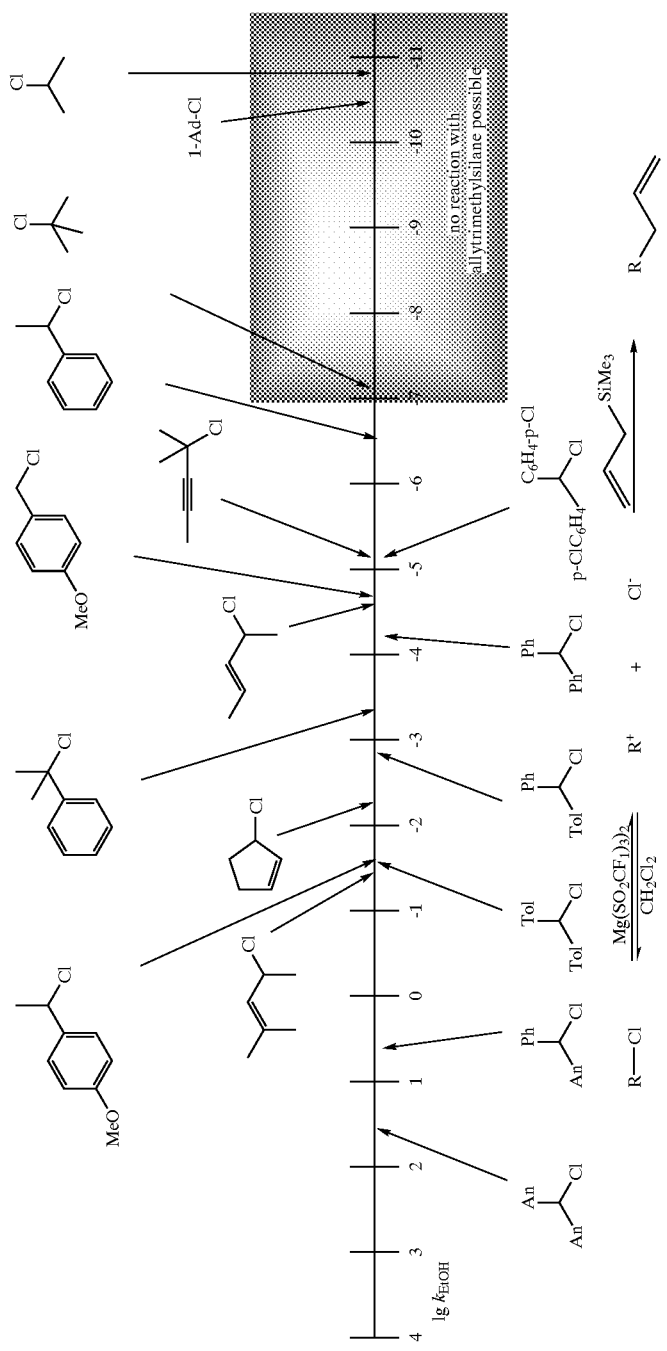

In accordance with the above reaction diagram (1.6), alkyl chlorides having an ethanolysis rate constant $k_{EtOH}$ (25° C.)$\geq 1\times 10^{-7}$ s$^{-1}$ give, with the Mg salts of the formula (1) used according to the invention, well-stabilized carbocations which react well with nucleophilic compounds having $N \geq 1.62$.

The relative reactivity of an electrophilic compound towards a nucleophilic compound in the reaction induced according to the invention can also be made by specifying the relative reactivity constant $k_{rel}$. $K_{rel}$ describes, for example, the relative reactivities of acetals and alkyl ethers towards allyltrimethylsilane in dichloromethane in the presence of catalytic amounts of ZnCl$_2$ etherate. Corresponding values can be taken from H. Mayr, J.-P. Dau-Schmidt, Chem. Ber. 1994, 127, 213–217.

Suitable compounds for the reactions induced according to the invention by the lithium salt of formula (1) suspended in non-coordinating solvents, preferably in dichloromethane, as catalyst, are preferably acetals or alkyl ethers, preferably methyl ether, whose relative reactivity constant krei is greater than or equal to that of benzaldehyde dimethylacetal. When the magnesium salt according to formula (1) is used, the acetals or alkyl ethers, preferably methyl ether, should have a relative reactivity constant krel which is greater than or equal to that of 1-tolyl-1-methoxyethane, where the nucleophilic compound should have a value $N \geq 1.62$ in all cases.

Dialkylacetals of any ketones or aldehydes, in particular $C_{1-C6}$-alkylacetals, particularly preferably dimethylacetals, mixed and cyclic dialkylacetals, can be used provided that they have the specified relative reactivity constant krel. This also applies to alkyl ethers of any hydroxyl compounds, where alkyl is preferably $C_1$–$C_6$-alkyl, in particular methyl or ethyl, or to N,O-acetals, i.e. to reaction products of any disubstituted amines, for example diisopropylamine or ethylphenylamine, with alcohols and aldehydes, in particular formaldehyde.

The tabulation (1.7) below sets forth selected methyl ethers and acetals which can be used as possible reaction partners of allyltrimethylsilane or more reactive nucleophiles ($N \geq 1.62$) in a suspension of LiC(SO$_2$CF$_3$)$_3$ in dichloromethane.

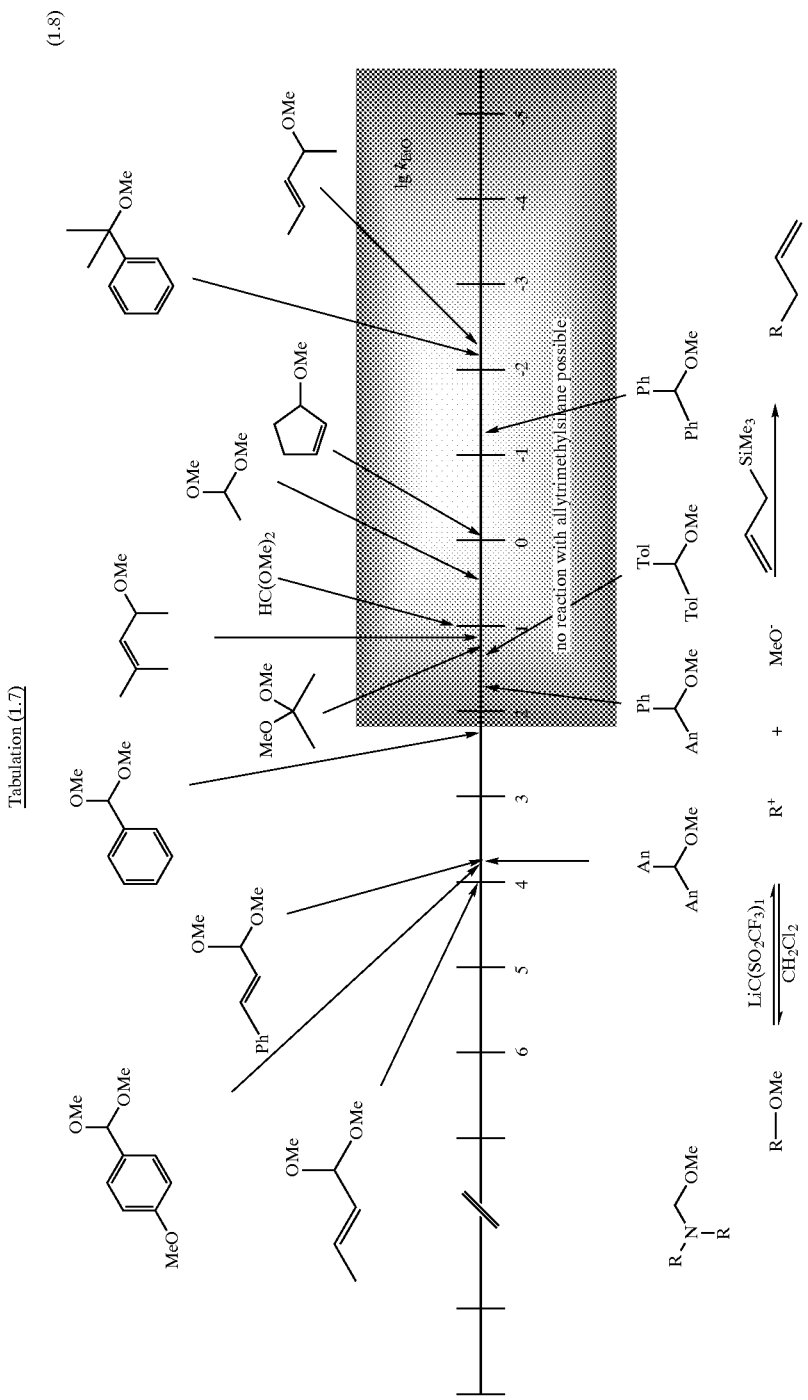

According to the above reaction diagram (1.8), reactions of acetals or methyl ethers whose relative reactivity constant $k_{rel} \geqq$ that of benzaldehyde dimethylacetal are possible.

The tabulation (1.9) below presents selected methyl ethers and acetals which can be used as possible reaction partners of allyltrimethylsilane or more reactive nucleophiles ($N \geqq 1.62$) in a suspension of $Mg(C(SO_2CF_3)_3)_2$ in dichloromethane.

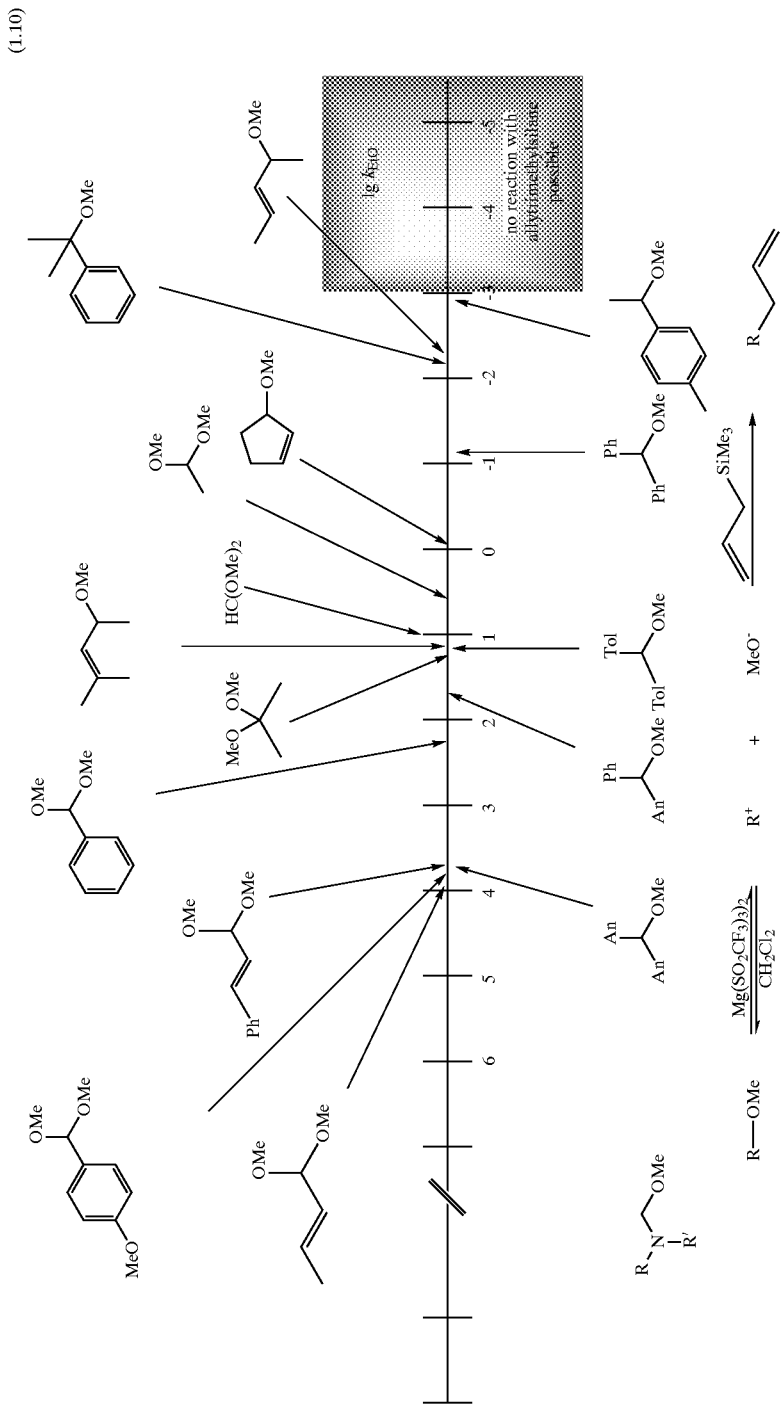

According to the above reaction diagram (1.10), methyl ethers or acetals can be reacted with nucleophiles having $N \geq 1.62$ provided that their relative reactivity constant $k_{drel}$ is greater than or equal to that of 1-tolyl-1-methoxyethane.

In the tabulations above, the abbreviations have the following meanings:
An 4-methoxyphenyl radical
Ph phenyl radical
Tol 4-methylphenyl radical
Me methyl radical The Lewis acid catalysts used according to the invention can also induce reactions of aldehydes whose reactivity is greater than or equal to that of benzaldehyde towards nucleophiles having a nucleophilicity $N \geq 5$, for example towards 1-phenyl-1-trimethylsiloxyethene, 1-trimethylsiloxycyclopentene or 1-methoxy-1-trimethylsiloxy-2-methyl-1-propene. Suitable aldehydes are in particular benzaldehyde or methoxybenzaldehyde. Preferably, suspensions of Li salts or Mg salts of the formula (1) are used as Lewis acid catalysts for this.

Preferably, this Lewis acid catalyst system is also used for inducing the reaction of ketones having a reactivity greater or equal to that of acetophenone towards nucleophiles having a nucleophilicity $N \geq 9$, for example methoxy-1-trimethylsiloxy-2-methyl-1-propene.

Preference is also given to the use of Li salts or Mg salts of the formula (1) as Lewis acid catalysts, preferably without addition of a solvent, for catalysing the reaction of carbonyl halides, in particular carbonyl chlorides or carbonyl bromides, whose reactivity is greater than or equal to that of benzoyl chloride towards nucleophiles having a nucleophilicity $N \geq 9$, for example 1-methoxy-2-methyl-1-trimethylsiloxypropane.

This also applies to the reaction of carboxylic anhydrides whose reactivity is greater than or equal to that of acetic anhydride towards nucleophiles having a nucleophilicity $N \geq -2$.

Li salts and Mg salts of the formula (1) also induce the [4+2]-cycloaddition of any dienes, for example 2,3-dimethyl-1,3-butadiene or cyclopentadiene. The olefins to be reacted with the dienes preferably bear electron-withdrawing substituents. Examples are methyl vinyl ketone or maleic anhydride. The cycloadditions generally proceed even at room temperature and are significantly accelerated in comparison with the uncatalysed reactions, generally by a factor of about 1.5. As an additional effect, the formation of the endo product is preferred. For [4+2] cycloadditions, the use of compounds of the formula (1) as a suspension in dichloromethane is preferred, where the concentration is 2–20 mol %, preferably 5–15 mol %, based on the dienophile to be activated.

The reactions are generally carried out at a temperature of from 0 to 60° C., preferably at from 10 to 30° C., under inert gas.

Preferably, tris(trifluoromethylsulfonyl)methane is suitable in a concentration of 0.5–10 mol %, preferably 1–5 mol %, based on the electrophilic acyl halide, preferably acyl chloride, for example acetyl chloride or benzoyl chloride, for the catalysis of Friedel Crafts acylations. Preferentially, the reaction temperatures of 60–105° C., preferably 80–110° C., should be maintained here.

This also applies to a corresponding intramolecular Friedel-Crafts acylation.

The reaction times are generally 2 to 250 hours, preferably from 3 to 72 hours, and particularly preferably from 12 to 48 hours.

The starting materials, electrophile and nucleophile, are used either as solution in the solvent or suspension medium of the catalyst compound of the formula (1), for example diethyl ether or dichloromethane, or, if they are liquid at the reaction temperature, as solvent-free substance.

The solvents or suspension media used for the reactions according to the invention are in each case anhydrous; they are dehydrated in a known manner.

The course of the reaction can be followed in each case by GC or HPLC.

After the reaction is completed, the reaction mixture is worked up in a customary manner, for example by hydrolysis with water and extraction with use of coordinating solvent or else by filtering off with use of non-coordinating solvent. The crude product can be purified, for example by chromatography, recrystallization or distillation.

The compound of the formula (1) is recovered either by filtering off the reaction mixture or by evaporating the aqueous phase produced after the hydrolysis of the reaction mixture. The compound (1) thus recovered can be purified in a customary manner, for example by suspension in a suitable solvent, for example dichloromethane/pentane (1/1 v/v) and subsequent filtration with suction. The compound is then dried in a conventional manner to constant weight, for example at 120–170° C./0.01 to 0.1 mbar, before it is reused.

Other reaction parameters must be taken from the general protocols for homogeneous or heterogeneous syntheses which are induced using the novel catalysts of the formula (1), in which case these instructions can be applied to all compounds of the formula (1) being used according to the invention in corresponding homogeneous or heterogeneous synthesis.

The invention further relates to the Mg compound of the formula (1) used according to the invention.

This Mg tris[(trifluoromethyl)sulfonyl]methanide can be obtained by reacting magnesium carbonate with tris (trifluoromethyl)sulfonyl)methane, preferably in stoichiometric amounts. As solubilizer, water was added until slight gas evolution started and the solids passed into solution. A highly viscous colourless solution was obtained. From this solution, the Mg salt of the formula (1) can be produced by drying. Since the salt is highly hygroscopic, it must be kept under protective gas.

EXAMPLES C

General Protocol 1 for Homogeneous Syntheses in Etherial $LiC(SO_2CF_3)_3$ Solutions The starting materials (50 mmol each) are added dropwise, either as liquids or as solutions in diethyl ether, to from 5 to 10 ml of a 0.03 m solution of $LiC(SO_2CF_3)_3$ in absolute diethyl ether under an inert gas atmosphere (nitrogen). The concentration of the Li salt is then from 1 to 10 mol %, based on the electrophile. The mixture is stirred at 20° C. up to the specified reaction time. To remove the lithium salt from the etherial phase 10 ml of water are added with vigorous stirring. The phases are then separated and the aqueous phase is extracted three times, each time with 10 ml of dichloromethane. The combined organic phases are dried over magnesium sulfate, filtered and the solvents are removed in vacuo. The remaining crude product is purified by recrystallization or distillation.

To recover the $LiC(SO_2CF_3)_3$, the aqueous phase is concentrated in vacuo and the crystalline salt is filtered off with suction. To remove any adhering organic substances, the $LiC(SO_2CF_3)_3$ is suspended in a mixture of dichloromethane and pentane (1/1 v/v) and then filtered off with suction. The resultant salt is dried to constant weight at 150° C./0.01 mbar.

General protocol 2 for heterogeneous syntheses using $LiC(SO_2CF_3)_3$ or $Mg(C(SO_2CF_3)_3)_2$ in $CH_2Cl_2$ The starting materials (50 mmol each), either as liquids or as solutions in dichloromethane, are added dropwise to the heterogeneous salt-dichloromethane mixture, to a suspension of from 0.05 to 0.50 g of the methanide in from 20 to 30 ml of dry dichloromethane under an inert gas atmosphere (nitrogen). The concentration of the Li salt in this case is from 1 to 10 mol %, based on the electrophile. The solution is stirred at 20° C. up to the time specified. After filtering the reaction mixture, the dichloromethane is removed in vacuo. The remaining crude product is purified by recrystallization or distillation. The methanide situated in the filtrate may be reused for other syntheses, after recrystallization.

General Protocol 3 for Homogeneous Systems Containing $HC(SO_2CF_3)_3$ Without Solvent Under an inert gas atmosphere (nitrogen), tris (trifluoromethylsulfonyl)methane (approximately 0.1 mmol) is added to a mixture of the starting materials (50 mmol each). The concentration of the $HC(SO_2CF_3)_3$ here is from 0.002–0.01 mmol/mmol of electrophile.

The reaction mixture is stirred at 20° C. or from 80 to 110° C. up to the specified time. After cooling the mixture to room temperature, 15 ml of water and 25 ml of diethyl ether are added, the phases are separated and the aqueous phase is extracted three times, each time with 10 ml of diethyl ether. The combined phases are dried over $MgSO_4$, filtered and the solvent is removed in vacuo. The remaining crude product is purified by recrystallization or distillation.

$HC(CO_2CF_3)_3$ is recovered as described in general protocol 1. The results of the reactions carried out in accordance with the above protocols are summarized in the following tables and diagrams, the following abbreviations being used:

An is 4-methoxyphenyl radical
Ad is the adenyl radical
Tol is the 4-methylphenyl radical

EXAMPLES 1–8

In accordance with protocol 1 or 2, lithium-tris (trifluoromethylsulfonyl)methanide-induced syntheses of alkyl chlorides were carried out using allyltrimethylsilane. The results of the reaction are compiled in Table 1.

TABLE 1

$1:LiC(SO_2CF_3)_3$-induced[a] reactions of alkyl chlorides with allyltrimethylsilane at 20° C.

| R-Cl | $K_{EtOH/s}{}^{-1}$ | Product | t/yield of $LiC(SO_2CF_3)_3$/-$CH_2Cl_2$ (suspension) | t/yield of $LiC(SO_2CF_3)_3$/-$Et_2O$- (0.03 M) |
|---|---|---|---|---|
| (4,4'-dimethoxybenzhydryl chloride) | 57.5 | (allylated product) | 3 h/99% | 3 h/89% |
| (4-methoxybenzhydryl chloride) | 0.501 | (allylated product) | 18 h/98% | 18 h/95% |
| (4-methylbenzhydryl chloride) | $1.23 \times 10^{-3}$ | (allylated product) | 14 h/85% | 20 h/33% |
| (benzhydryl chloride) | $5.37 \times 10^{-5}$ | (allylated product) | 120 h/30% | 120 h/0% |

[a]Use of mol % with respect to alkyl chloride,
[b]ethanolysis constant of the alkyl chlorides

EXAMPLES 9–12

In accordance with protocol 2, lithium-tris (trifluoromethylsulfonyl)methanide-induced syntheses of acetals and methyl ethers were carried out using allyltrimethylsilane. The results are summarized in Table 2

TABLE 2

Reactions of methyl ethers and acetals with
allyltrimethylsilane in a suspension of LiC(SO$_2$CF$_3$)$_3$[a]
in dichloromethane (20° C.)

| R-OMe | t/h | Product | Yield |
|---|---|---|---|
| 4,4'-dimethoxybenzhydryl methyl ether (bis(4-methoxyphenyl)methoxymethane) | 130 | 1,1-bis(4-methoxyphenyl)but-3-ene (with OMe on central C) | 90% |
| anisaldehyde dimethyl acetal (4-MeO-C$_6$H$_4$-CH(OMe)$_2$) | 120 | 1-(4-methoxyphenyl)-1-methoxybut-3-ene | 78% |
| tolylaldehyde dimethyl acetal (4-Me-C$_6$H$_4$-CH(OMe)$_2$) | 130 | 1-(4-methylphenyl)-1-methoxybut-3-ene | 57% |
| benzaldehyde dimethyl acetal (Ph-CH(OMe)$_2$) | 240 | 1-phenyl-1-methoxybut-3-ene | 35% |

[a]Use of 5 mol % with respect to methyl ether or acetal.

While bis(4-methoxyphenyl)methyl chloride may be quantitatively reacted with allyltrimethylsilane in a suspension of lithium tris(trifluoromethylsulfonyl)methanide in dichloromethane to give the allylated product within three hours (Table 1), the analogous methyl ether bis(4-methoxyphenyl)methoxymethane with allyltrimethyl-silane only gives the allylated product (Table 2) in 90% yield after 120 hours. The lithium tris(trifluoromethylsulfonyl)-methanideinduced reaction of anisaldehydedimethylacetal with allyltrimethylsilane gives the corresponding homoallyl alcohol in 78% yield within 130 hours. The less reactive tolylaldehyde dimethylacetal and benzaldehydedimethyl acetal react within 130 and 240 hours, respectively, in significantly poorer yields to form the corresponding homoallyl ethers.

EXAMPLES 13–14

According to protocol 2, lithium-tris (trifluoromethylsulfonyl)methanide-induced syntheses of N,O-acetals were carried out using 1-methoxy-2-methyl-1-trimethylsiloxypropane.

The ionization capacity of a suspension of lithium tris (trifluoromethylsulfonyl)methanide in dichloromethane is sufficiently great to generate iminium ions from N,O-acetals. The reaction of the N,O-acetals with 1-methoxy-2-methyl-1-trimethylsiloxypropene induced by a suspension of lithium tris(trifluoromethylsulfonyl)methanide in dichloromethane gives the corresponding amino esters in very good yields (Table 3).

TABLE 3

Reactions of N,O-acetals with 1-methoxy-2-methyl-1-trimethylsiloxypropene in a suspension of LiC(SO$_2$CF$_3$)$_3$[a] in dichloromethane (20° C.)

| R-OMe | t/h | Product | Yield |
|---|---|---|---|
| (iBu)(iBu)N-CH$_2$-OMe | 35 | (iBu)(iBu)N-CH$_2$-C(Me)$_2$-C(O)-OMe | 89% |
| Ph(Et)N-CH$_2$-OMe | 48 | Ph(Et)N-CH$_2$-C(Me)$_2$-C(O)-OMe | 88% |

[a]Use of 5 mol % with respect to N,O-acetal.

EXAMPLES 15–17

In accordance with the general protocol 2, lithium-tris(trifluoromethylsulfonyl)methanide-induced reactions of benzaldehyde were carried out using the nucleophiles specified in Table 4.

TABLE 4

Lithium-tris(trifluoromethylsulfonyl)-methanide-induced reactions[a] of benzaldehyde in dichloromethane (20° C.)

| Nucleophile | N[b] | t/h | Product | Yield |
|---|---|---|---|---|
| CH$_2$=C(Me)-OSiMe$_3$ | 5.95 | 40 h | Ph-CH(OSiMe$_3$)-CH$_2$-C(O)-Me | 17% |
| CH$_2$=C(Me)-CH$_2$-SnBu$_3$ | 7.92 | 23 h | Ph-CH(OSnBu$_3$)-CH$_2$-C(Me)=CH$_2$ | 75% |
| (Me)(OMe)C=C(Me)-OSiMe$_3$ | 9.49 | 3 h | Ph-CH(OSiMe$_3$)-C(Me)$_2$-C(O)-OMe | 60% |

[a]5 mol % of LiC(SO$_2$CF$_3$)$_3$ with respect to benzaldehyde were used;
[b]nucleophilicity parameter N

EXAMPLE 18

In accordance with the general protocol 2, acetophenone was reacted with 1-methoxy-2-methyl-1-trimethylsiloxypropene according to the following reaction diagram

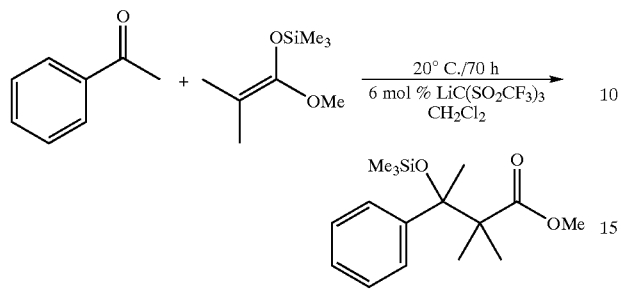

The yield of the product was 44%

EXAMPLE 19
Reaction of Acetic Anhydride

If a mixture of acetic anhydride and anisole (N=1.56) is heated in the presence of 6 mol % of lithium tris(trifluoromethylsulfonyl)methanide for 48 hours at 120° C. without the addition of a solvent, the acylation product is isolated in 41% yield.

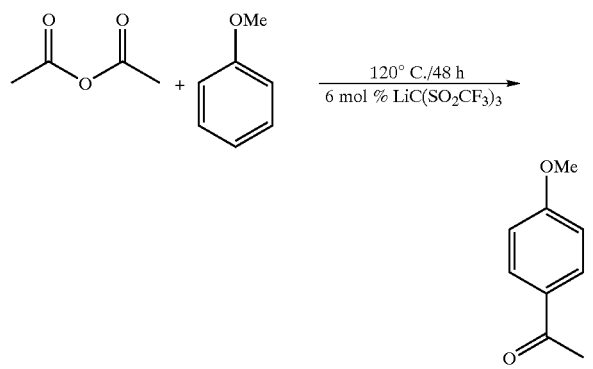

EXAMPLE 20
Reaction of Benzoyl Chloride

Under similar reaction conditions to those in Example 19, benzoyl chloride successfully reacts with the significantly more nucleophilic 1-methoxy-2-methyl-1-trimethylsiloxypropene (N=9.49). The acylation product is obtained within 24 hours in 72% yield.

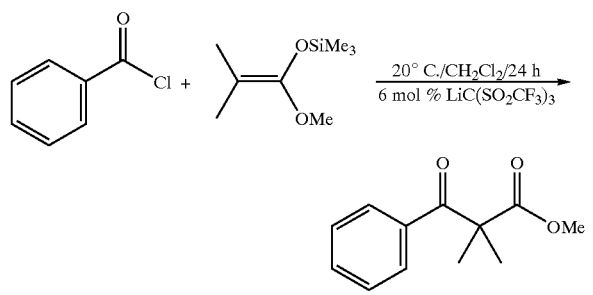

EXAMPLES 21–23
Lithium-tris(trifluoromethylsulfonyl)methanide-induced [4+2]-cycloadditions Cycloaddition Using 2,3-dimethyl-1,3-butadiene In the presence of 15 mol % of lithium tris(trifluoromethylsulfonyl)methanide in dichloromethane, within 60 hours the [4+2]-cycloadduct is obtained in 50% yield from 2,3-dimethyl-1,3-butadiene and methyl vinyl ketone. The activating effect of lithium tris(trifluoromethylsulfonyl)methanide on this cycloaddition is significantly less intensively expressed in diethyl ether because of coordinating interactions between the Lewis acid lithium cation and the oxygen of the ether. The cycloadduct is obtained after 20 hours of reaction time in only 2% yield (Table 5). For comparison, the uncatalysed reaction takes 4000 hours (167 days) at 20° C. for quantitative conversion of the starting materials.

TABLE 5

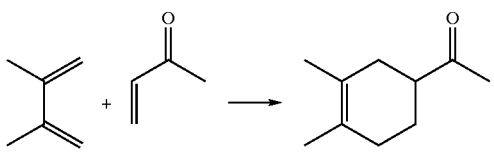

Reaction of 2,3-dimethyl-1,3-butadiene with methyl vinyl ketone at 20° C.

| Solvent/catalyst | $t_{Rkt}$/h | Conversion rate |
|---|---|---|
| Et$_2$O/LiC(SO$_2$CF$_3$)$_3$ (5 mol %[a]) | 20 | 2% |
| CH$_2$Cl$_2$/LiC(SO$_2$CF$_3$)$_3$ (15 mol %[a]) | 60 | 50% |

[a]relative amount of substance of the lithium salt with respect to methyl vinyl ketone.

Cycloaddition using cyclopentadiene according to the reaction diagram below

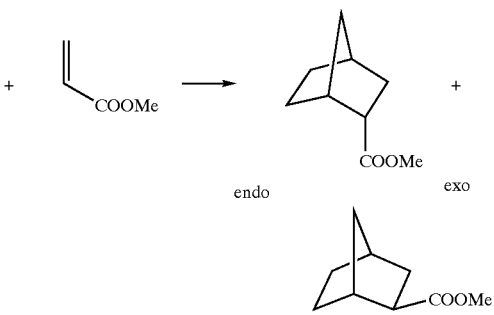

The reaction of cyclopentadiene with methyl acrylate in accordance with the above conditions is accelerated by the factor 1.5 by addition of 2 mol % of lithium tris(trifluoromethylsulfonyl)methanide with respect to methyl acrylate to the solvent dichloromethane. The endo/exo ratio is 4.4/1.

EXAMPLES 24–27
A) Preparation of Magnesium tris(trifluoromethylsulfonyl)methanide 0.8153 g (1.979 mmol) of tris(trifluoromethylsulfonyl)methane are combined with 0.0962 g (0.198 mmol) of basic magnesium carbonate (4 MgCO$_3$.Mg(OH)$_2$.5H$_2$O) and this is mixed with 0.3 ml of water, with CO$_2$ being released. The high-viscosity liquid is stirred for 3 h at room temperature. The colourless crystalline powder obtained after removing the solvent in vacuo is dried for 2 days at 50° C. (1.2×10$^-$2mbar). The magnesium salt is obtained as colourless highly hygroscopic crystallites.

Yield: 96% (0.185 g) with melting point 141–143° C.

B) In accordance with protocol 2, reactions of alkyl chlorides using allyltrimethylsilane which were induced by magnesium tris(trifluoromethylsulfonyl)methanide prepared in accordance with A) were carried out. The results are given in Table 6.

TABLE 6

Reactions of alkyl chlorides with allyltrimethylsilane in a suspension of $Mg(C(SO_2CF_3)_3)_2$ in dichloromethane (20° C)

| R-Cl | $\kappa_{EtOH}{}^{[a]}/s^{-1}$ | $Mg(C(SO_2CF_3)_3)_2$ mol % | t/h | Yield |
|---|---|---|---|---|
| 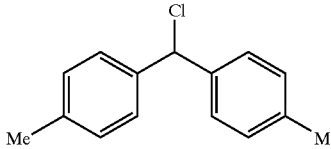 | $2.04 \times 10^{-2}$ | 10<br>5<br>1 | 18<br>22<br>24 | 93%<br>88%<br>80% |
| 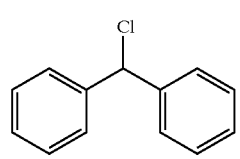 | $5.37 \times 10^{-5}$ | 10<br>5<br>1 | 24<br>24<br>48 | 91%<br>76%<br>96% |
| 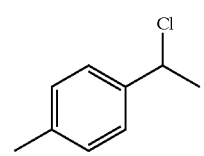 | $9.12 \times 10^{-6}$ | 10<br>1 | 22<br>24 | 93%<br>81% |
| 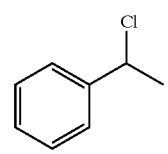 | $1.66 \times 10^{-7}$ | 10 | 22 | 41% |

[a]ethanolysis constant of the alkyl chlorides

EXAMPLES 28–29

In accordance with protocol 2, reactions of methyl ethers with allyltrimethylsilane were carried out using the magnesium tris(trifluoromethylsulfonyl)methanide prepared according to Example 24–27 A) The results are summarized in Table 7.

TABLE 7

Reactions of methyl ethers with allyltrimethylsilane in a suspension of $Mg(C(SO_2CF_3)_3)_2$ in dichloromethane (20° C.).

| R-OMe | $Mg(C(SO_2CF_3)_3)_2$ mol % | t/h | Product | Yield |
|---|---|---|---|---|
| 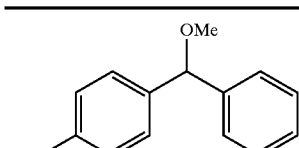 | 10<br>5<br>1 | 24<br>45<br>48 | | 96%<br>92%<br>84% |

TABLE 7-continued

Reactions of methyl ethers with allyltrimethylsilane in a suspension of $Mg(C(SO_2CF_3)_3)_2$ in dichloromethane (20° C.).

| R-OMe | $Mg(C(SO_2CF_3)_3)_2$ mol % | t/h | Product | Yield |
|---|---|---|---|---|
| 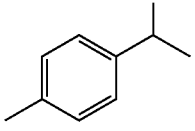 | 10<br>5<br>1 | 72<br>72<br>72 | | 62%<br>56%<br>43% |

EXAMPLES 30–31

In accordance with protocol 3, tris(trifluoromethylsulfonyl)methane-induced Friedel-Crafts acylations were carried out using the specified benzene derivatives according to the reaction diagram below. The results are given in Table 8.

Syntheses of acetyl chloride using benzene derivatives

TABLE 8

Reactions of acetyl chloride with benzene derivatives.

| X | Y | T/° C. | t/h | H(SO$_2$CF$_3$)$_3$ mol % | Yield |
|---|---|---|---|---|---|
| H | OMe | 20 | 48 | 5 | 10% |
|   |   | 85 | 20 | 5 | 44% |
|   |   | 100 | 20 | 1 | 26% |
| Me | Me | 20 | 24 | 5 | 5% |
|   |   | 110 | 16 | 5 | 32% |
|   |   | 110 | 43 | 1 | 10% |

EXAMPLES 32–34

In accordance with protocol 3, tris(trifluoromethylsulfonyl)methane-induced reactions of benzoyl chloride with benzene derivatives were carried out in accordance with Table 9. The results are given in Table 9.

TABLE 9

Reactions of benzoyl chloride with benzene derivatives.

| X | Y | T/° C. | t/h | H(SO$_2$CF$_3$)$_3$ mol % | Yield |
|---|---|---|---|---|---|
| H | OMe | 100 | 15 | 5 | 62% |
|   |   | 100 | 43 | 1 | 63% |
| Me | Me | 110 | 15 | 5 | 87% |
|   |   | 110 | 20 | 1 | 67% |
| H | Me | 110 | 20 | 5 | 75% |
|   |   | 110 | 48 | 1 | 68% |

EXAMPLES 35–36

Intramolecular Friedel-Crafts Acylations

In accordance with protocol 3, the intramolecular Friedel-Crafts acylation of o-benzylbenzoic acid or o-benzoylbenzoic acid to give anthrone or anthraquinone, respectively, was carried out using tris(trifluoromethylsulfonyl)methane as catalyst. The yield of the products was 45%.

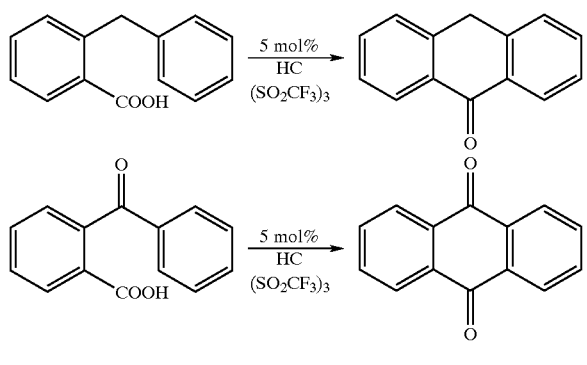

TABLE 10
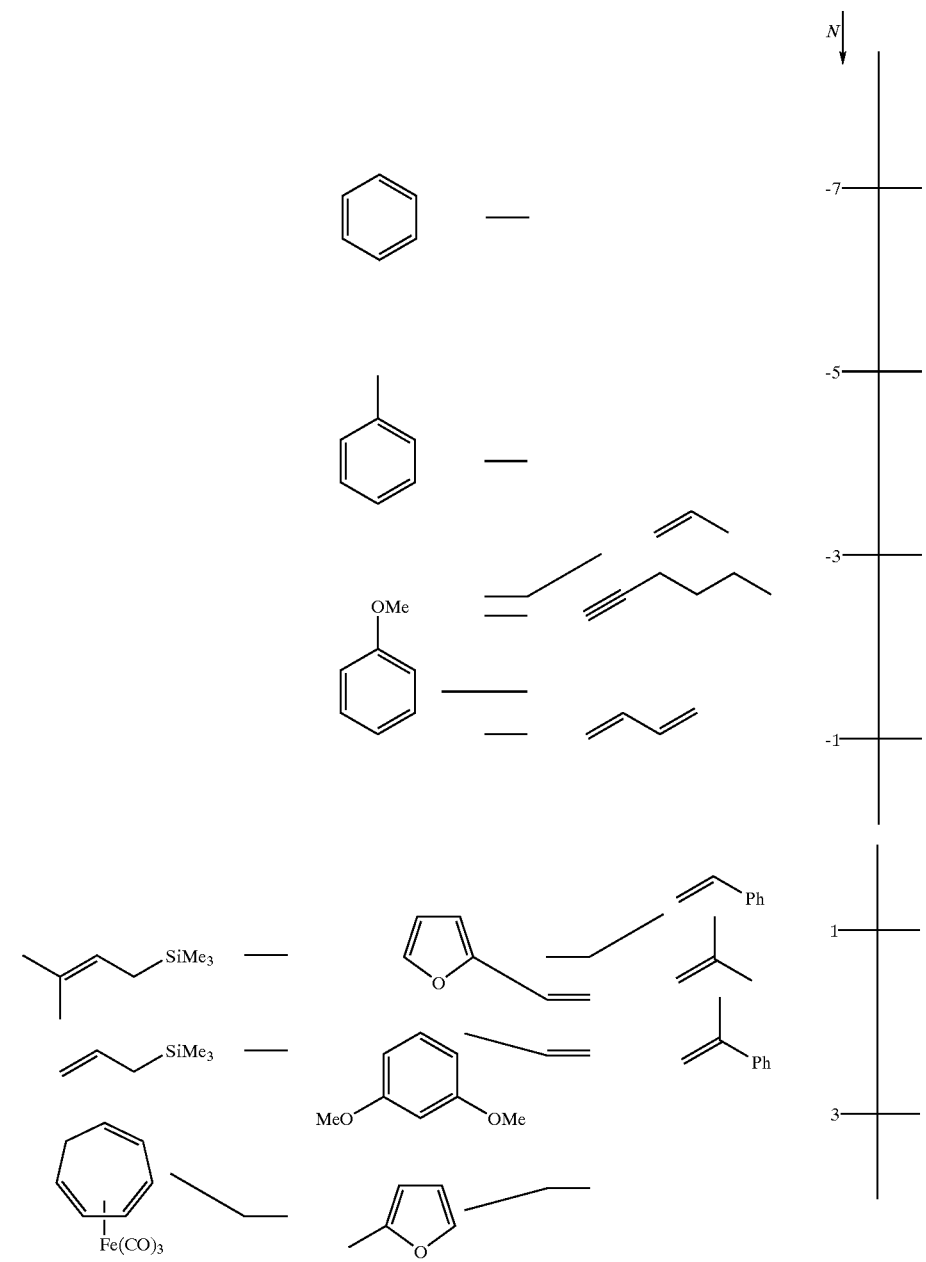

TABLE 10-continued

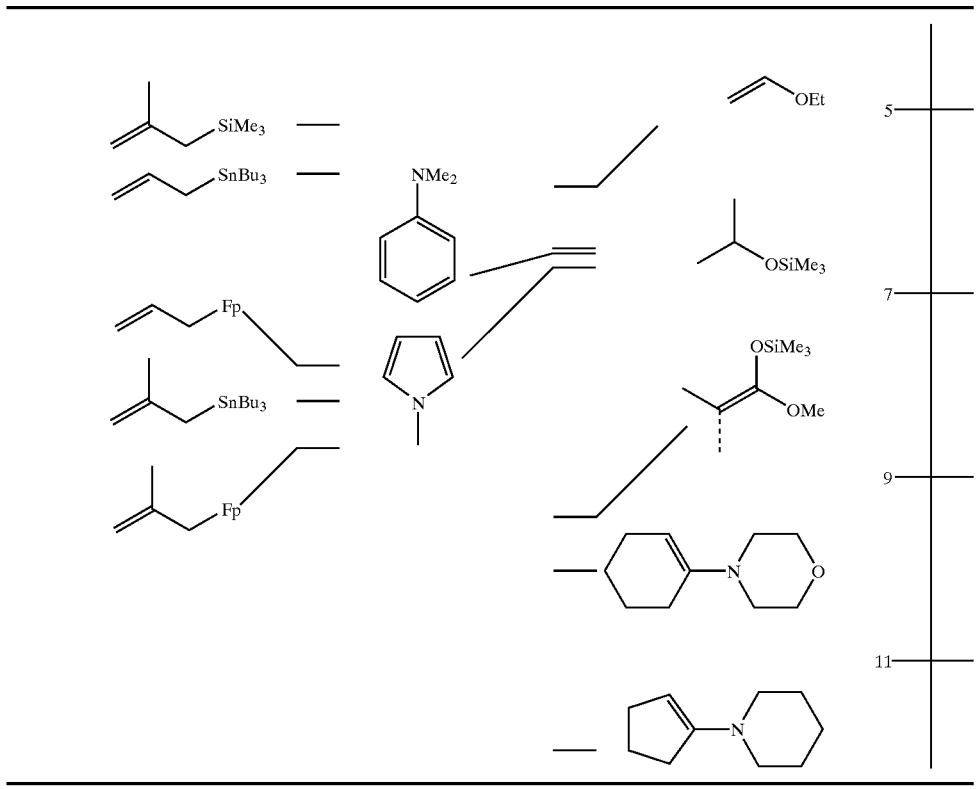

What is claimed is:

1. A method of catalyzing a carbon-carbon bond-forming chemical reaction, comprising as a catalyst using at least one compound of the formula (1)

$$M^{+x}(C(SO_2CF_3)_3)_x \qquad (1)$$

wherein x is 1 or 2,

M is a hydrogen atom or alkali metal atom when x is 1, or is an alkaline earth metal atom when x is 2.

2. The method according to claim 1, wherein M is hydrogen, lithium, sodium, potassium, magnesium or calcium, in particular hydrogen, lithium or magnesium.

3. The method of claim 1, wherein compounds of the formula (1) are used as a homogeneous solution in coordinating, organic solvents.

4. The method of claim 1, wherein the compounds of the formula (1) are used as a suspension in non-coordinating organic solvents.

5. The method of claim 1, wherein the reaction employs Lewis-acid-activatable electrophiles.

6. The method of claim 1, wherein lithium tris (trifluoromethylsulfonyl)methanide, suspended in a non-coordinating solvent, is used as Lewis acid catalyst in the reaction of alkyl halides, having an ethanolysis rate $k_{EtOH}$ (25° C.)>1×10$^{-5}$ s$^{-1}$ with nucleophiles having a nucleophilicity N≧1.

7. The method of claim 1, wherein lithium tris (trifluoromethylsulfonyl)methanide, dissolved in a coordinating, organic solvent, is used as Lewis acid catalyst in the reaction of alkyl halides, having an ethanolysis rate $k_{EtOH}$ (25° C.)>1×10$^{-7}$ s$^{-1}$ with nucleophiles having a nucleophilicity N≧1.

8. The method of claim 1, wherein magnesium tris (trifluoromethylsulfonyl)methanide, suspended in a non-coordinating solvent, is used in the reaction of alkyl halides, having an ethanolysis rate $k_{EtOH}$ (25° C.)>1×10$^{-7}$ s$^{-1}$ with nucleophiles having a nucleophilicity N≧1.

9. The method of claim 1, wherein lithium tris (trifluoromethylsulfonyl)methanide is used as suspension in non-coordinating solvents, and the reaction of alkyl ethers or alkyl acetals having a relative reactivity $K_{rel}$, which is greater than that of benzaldehyde dimethylacetal, with nucleophiles having a nucleophilicity N≧1 is catalysed.

10. The method of claim 1 wherein magnesium tris (trifluoromethylsulfonyl)methanide is used as suspension in a non-coordinating solvent, and the reaction of alkyl ethers or alkyl acetals having a relative reactivity $K_{rel}$, which is greater than that of 1-tolyl-1-methoxyethane, with nucleophiles having a nucleophilicity N≧1 is catalysed.

11. The method of claim 1, wherein lithium tris (trifluoromethylsulfonyl)methanide or magnesium tris (trifluoromethylsulfonyl)methanide is used as suspension in non-coordinating solvents, and the reaction of aldehydes having a reactivity which is at least equal to or greater than that of benzaldehyde with nucleophiles having a nucleophilicity N≧5 is catalysed.

12. The method of claim 1, wherein lithium tris (trifluoromethylsulfonyl)methanide or magnesium tris (trifluoromethylsulfonyl)methanide is used as suspension in non-coordinating solvents, and the reaction of ketones having a reactivity which is at least equal to or greater than that of acetophenone with nucleophiles having a nucleophilicity N≧9 is catalysed.

13. The method of claim 1, wherein lithium tris(trifluoromethylsulfonyl)methanide or magnesium tris(trifluoromethylsulfonyl)methanide is used and the reaction of acyl halides, whose reactivity is equal to or greater than that of benzoyl chloride towards nucleophiles having a nucleophilicity $N \geqq 9$ is catalysed.

14. The method of claim 1, wherein lithium tris(trifluoromethylsulfonyl)methanide or magnesium tris(trifluoromethylsulfonyl)methanide is used and the reaction of carboxylic anhydrides whose reactivity is equal to or greater than that of acetic anhydride towards nucleophiles having a nucleophilicity $N \geqq -2$ is catalysed.

15. The method of claim 1, wherein tris(trifluoromethylsulfonyl)methane is used and Friedel-Crafts acylations are catalysed.

16. The method of claim 5, wherein the electrophiles are alkyl halides, dialkylacetals, alkyl ethers, N, O-acetals, ketones, aldehydes, acyl halides or carboxylic anhydrides with nucleophiles or in [4+2]-cycloadditions.

17. The method of claim 4, wherein the non-coordinating solvent is dichloromethane.

18. The method of claim 3, wherein the organic solvent is diethyl ether.

\* \* \* \* \*